Figure 1:
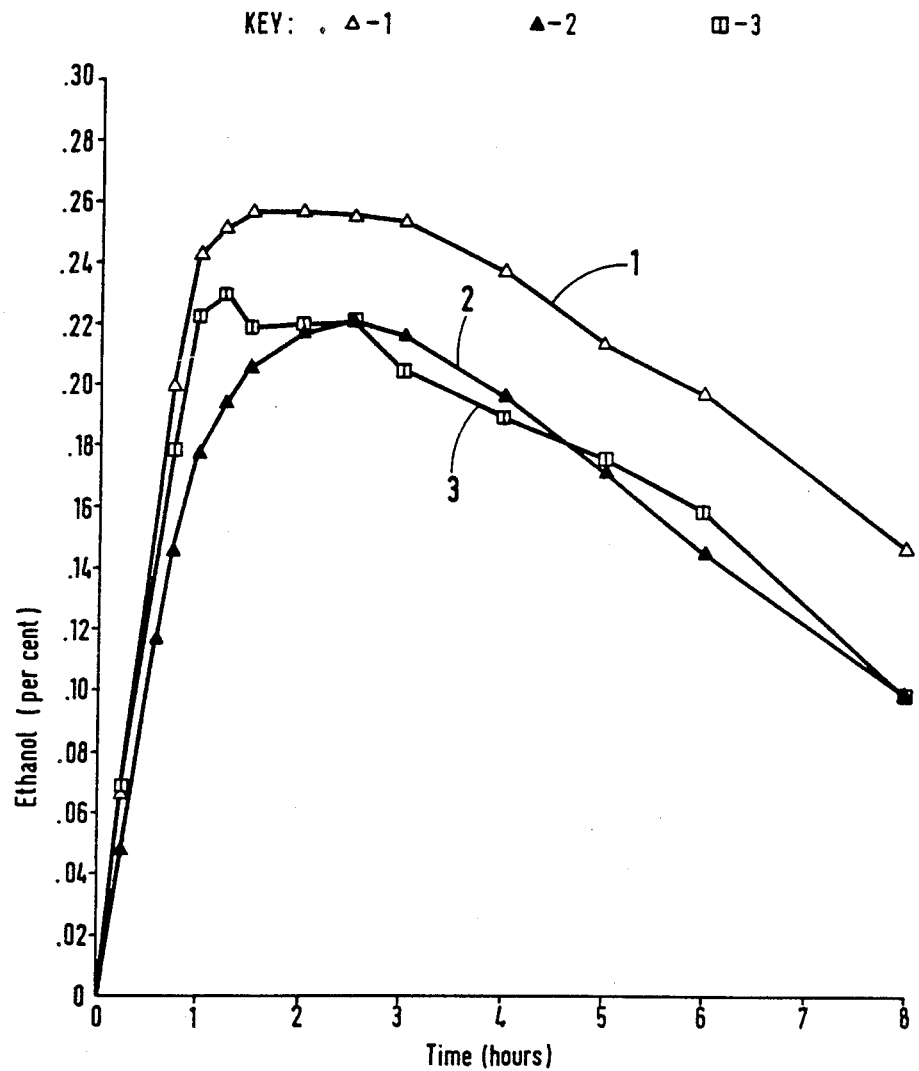

United States Patent [19]

Wren

[11] Patent Number: 4,877,601
[45] Date of Patent: Oct. 31, 1989

[54] ADSORBENT COMPOSITION

[75] Inventor: John J. Wren, London, England

[73] Assignee: Watney Combe Reid & Truman Limited, London, England

[21] Appl. No.: 27,028

[22] PCT Filed: Jul. 1, 1986

[86] PCT No.: PCT/GB86/00386
§ 371 Date: Feb. 18, 1987
§ 102(e) Date: Feb. 18, 1987

[87] PCT Pub. No.: WO87/00049
PCT Pub. Date: Jan. 15, 1987

[30] Foreign Application Priority Data

Jul. 2, 1985 [GB] United Kingdom ............... 8516670

[51] Int. Cl.$^4$ .............................................. A61K 33/06
[52] U.S. Cl. ...................................... 424/10; 424/684; 514/811; 514/823
[58] Field of Search ...................... 424/10, 125, 154; 514/811, 823, 770

[56] References Cited

U.S. PATENT DOCUMENTS 4,537,771 8/1985 Greb et al. ........................ 424/157
4,627,972 12/1986 Gioffre et al. ...................... 424/44

FOREIGN PATENT DOCUMENTS 101254 2/1984 European Pat. Off. .

OTHER PUBLICATIONS

Synthesis of High-Silica Aluminosilicate Zeolites Jacobs et al., Studies in Surface Science and Catalysis, vol. 33, pp. 103–106, 1987.
"Zeolites as Adsorbents for Alcohols from Aqueous Solutions", Haegh, Zeolites ©1985, pp. 605–609.

Primary Examiner—Douglas W. Robinson
Assistant Examiner—Raymond J. Henley, III
Attorney, Agent, or Firm—Ladas & Parry

[57] ABSTRACT

Use of a physiologically inert hydrophobic molecular sieve material to lower the blood alcohol level in the human body in the form of an edible composition or a suppository, the material having a pore size permitting the absorption of ethanol but preventing the absorption of larger molecules with lipophilic character. The material may be a crystalline zeolitic material such as Silicalite or ZSM5.

6 Claims, 2 Drawing Sheets

ADSORBENT COMPOSITION

This invention relates to compositions which assist in the removal of alcohol from human systems.

The problem of lowering alcohol content from a human being particularly in the blood is one which has received considerable attention without any great success in solving the problem.

Alcohol can remain in the blood for many hours after original ingestion. Various factors influence the level of blood alcohol found after the ingestion of alcoholic beverages and alcohol-containing foods. These include:-

(i) Quantity of alcohol consumed.
(ii) Speed of consumption.
(iii) Intake of solid food before, during or after alcohol consumption.
(iv) Ratio of water to alcohol consumed.
(v) Consumption of additional stimulants and drugs.
(vi) 'Liver training', meaning an enhancement in katabolic enzymes in response to prior ingestion of alcohol.
(vii) Disease.
(viii) Metabolic rate, which is dependant upon physical activity and emotional state.

However, the degree to which such factors influence blood-alcohol levels seems to vary widely according to individual circumstances. Injudicious consumption of alcohol leads to a demand for products capable of reducing its concentration in the body, for example, (a) to conform with "drink-and-drive" legislation, (b) to avert hangovers, or (c) in medical emergencies.

Proposals have been made to accelerate the metabolism of the alcohol so as to lead to early removal from the system. However, biologically active compounds have proved either ineffective or erratic and unpredictable. Thus fructose is believed to accelerate the metabolism of ethanol and compositions containing either fructose or sucrose have been suggested. The ingredients of one such product, on sale in the USA, are declared as: vitamin C; spirulina micro algae, papaya powder, fructose, caffeine, cayenne pepper, binding agents. The most popular ingredients of such products in general include vitamins and fructose, both of which have been shown in specific circumstances to produce the desired effect. The effectiveness of these has been challenged. Even to the extent that some effectiveness has been shown, it is erratic and extremely personal as to whether an individual will in fact find a lowering of alcohol as a result of ingestion of fructose. At best, the results achieved are highly variable and therefore inadequate for the requirements. Further disadvantages of such products are their side-effects, for example the heavy calorie load of fructoe at the recommended dose. Alcohol-degrading enzymes have been considered, but rejected because degradation products, such as aceteldehyde, tend to be more toxic than alcohol itself.

Absorbing systems have been suggested such as charcoal. Here again, however, any evidence indicates either little or no effect or very unpredictable effect. Part of the problem with charcoal is that it tends not to be specific in its absorption and there is interference from other materials in the stomach and intestine some of which either prevent absorption of alcohol or result in release of alcohol once absorbed.

Generally speaking because of the very complex nature of the contents of the intestines it is believed that a simple physical absorption system would not be likely to give satisfactory or predictable absorption of alcohol sufficient to lower the alcohol content in the blood. Moreover there was no reason to believe that simple absorption from the stomach contents might affect the presence of alcohol elsewhere in the human body.

It has now been surprisingly found that one particular type of absorbent does effectively lower the body content of alcohol particularly the alcohol content of the blood and to do so on a predictable basis.

In the present invention therefore there is provided a composition in edible form which contains a physiologically inert hydrophobic molecular sieve material, particularly a crystalne zeolite, which has a pore size such as to permit the absorption of ethanol but the exclusion of other organic materials present in the blood or intestines. Such zeolites have hitherto been known as industrial materials. For ingestion they would have to be prepared in a form suitable for administration for example by dispersion in an edible or physiologically acceptable base and particularly in dosage unit form having regard to the amount of alcohol to be absorbed. The invention also encompasses a method of producing a medicament comprising said zeolite for the purpose of administration to a human being to counteract the effects of the presence of alcohol in the human body.

Apart from the general desire to lower blood alcohol such a system might be important where the patient has to be treated rapidly to lower blood alcohol where other medical treatment is mandated, for example, in traffic accidents.

The administration of such molecular sieves, particularly hydrophobic zeolites, to human beings has not hitherto been suggested. The invention therefore also includes said molecular sieve, particularly a crystalline aluminosilicate zeolite or an edible or physiological composition containing such molecular sieve, e.g. zeolite, for use in a method for the treatment of the human body to lower the content of alcohol in the body.

The sieve material, e.g. a zeolite could be combined with other inert substances particularly if intended to make it more palatable. Since a reasonable bulk of the composition might be necessary, it will probably more easily administered in liquid dispersion in an inert carrier such as simple water or a carrier intended to alleviate other conditions in the stomach.

It is surprising to find that this particular zeolite is effective in that other siliceous materials for example amorphous silica, bentonite and kaolin are frequently administered for the relief of stomach problems but no effect on alcohol absorption has hitherto been noted. One effect of the absorbent may be that, not only does it reduce the alcohol content in the intestine, but because of equilibration between the intestine contents and the blood steam, in a sense, it draws back into the stomach alcohol already absorbed into the rest of the body. The alcohol absorbed appears to be permanently absorbed into the pores of the zeolite and is excreted from the body through the intestines and therefore does not, as in other systems, interfere with the operation of the liver and kidneys or the urinary system. The amount of the zeolite or composition containing the zeolite necessary to reduce alcohol would depend on the degree of production desired but assuming the blood content is not significantly above the current legal limits then administration of from 25 to 50 grammes of the zeolite might be sufficient to lower the alcohol content to below the legal limit (legal limit under UK law is 0.08% blood alcohol concentration). Much would depend however on the size of the person ingesting the zeolite, the actual blood alcohol content and certain other specific factors concerning a particular individual.

Since hangovers are attributed, at least in part, to acetaldehyde (a metabolite of ethanol), and acetaldehyde is strongly absorbed by these absorbents, the latter are expected to have an additional function in relieving the after-effects of excessive alcohol consumption.

A zeolite which can be employed is a hydrophobic zeolite having a pore size sufficient to absorb alcohol but not so great that other interfering organic materials will also be absorbed.

Materials which fulfil this aim are zeolitic molecular sieves of a type having hydrophobic properties. Such materials are commonlly available under various names including Silicalite and ZSM5 and consist essentially of a porous crystalline structure of silicon and oxygen atoms, usually with aluminium in minor quantity, and sometimes also with minor quantities of other elements such as boron. For the purpose of this invention, however, their essential property is that the crystal structure contains pore cavities which are (a) hydrophobic, (b) large enough to contain molecules of ethanol, and (c) small enough to exclude larger molecules with lipophilic character—for example, fatty acids—that occur in significant concentration in the digestive system.

An outline of the structural chemistry of these materials can be found in R. M. Barrer's book, "Hydrothermal Chemistry of Zeolites" (Academic Press, 1982). The selective adsorption properties, for molecules with lipophilic character, is known—see papers by R. M. Desau and others in "Adsorption and Ion Exchange with Synthetic Zeolites" (editor Flank, WH; monograph No. 135 in the American Chemical Society Symposium Series).

The application of these zeolites to the recovery of ethanol from aqueous solutions is also known—see paper by F. A. Farhadpour et al (European Brewery Convention Monograph—1X, Symposium on Biotechnology, 1983, pages 203-217) and European Patent Publication 0101254.5. The present invention, however, aims to reject ethanol from a system and not to recover it.

A particular synthetic crystalline aluminosilicate zeolite with a high silica content having a molar ratio of silica to alumina in a range of 12:1 to 300:1 has been suggested in European Patent Specification 0101254 for the separation of ethanol from commercial systems and such zeolite would be usable in any present invention when rendered into forms suitable for absorption by human beings. Usable in the present invention, however, would be generally hydrophobic crystalline molecular sieves in which the pore size is sufficient to accommodate ethanol but reject larger hydrophobic molecules. Inherently such compositions must be inert so as to avoid breakdown in the intestine.

In another embodiment of the invention there is provided a system containing such a molecular sieve, particularly said zeolite, and through which blood from a patient can be passed. This can be of importance in assisting in the reduction of the alcohol content of the blood for a patient where such reduction is urgently necessary for the purpose of other treatments as for example in accidents. Such a system could be a simple bag into which blood in introduced and returned to the patient. The system could be provided with zeolite in one portion and a semipermeable membrane which separates the blood from the molecular sieve but permits diffusion of alcohol to the molecular sieve.

The composition of the invention could be in the form of compositions which would be introduced into the intestinal system for example as suppositories or other compositions suitable for introduction through the rectum.

Figure 2:
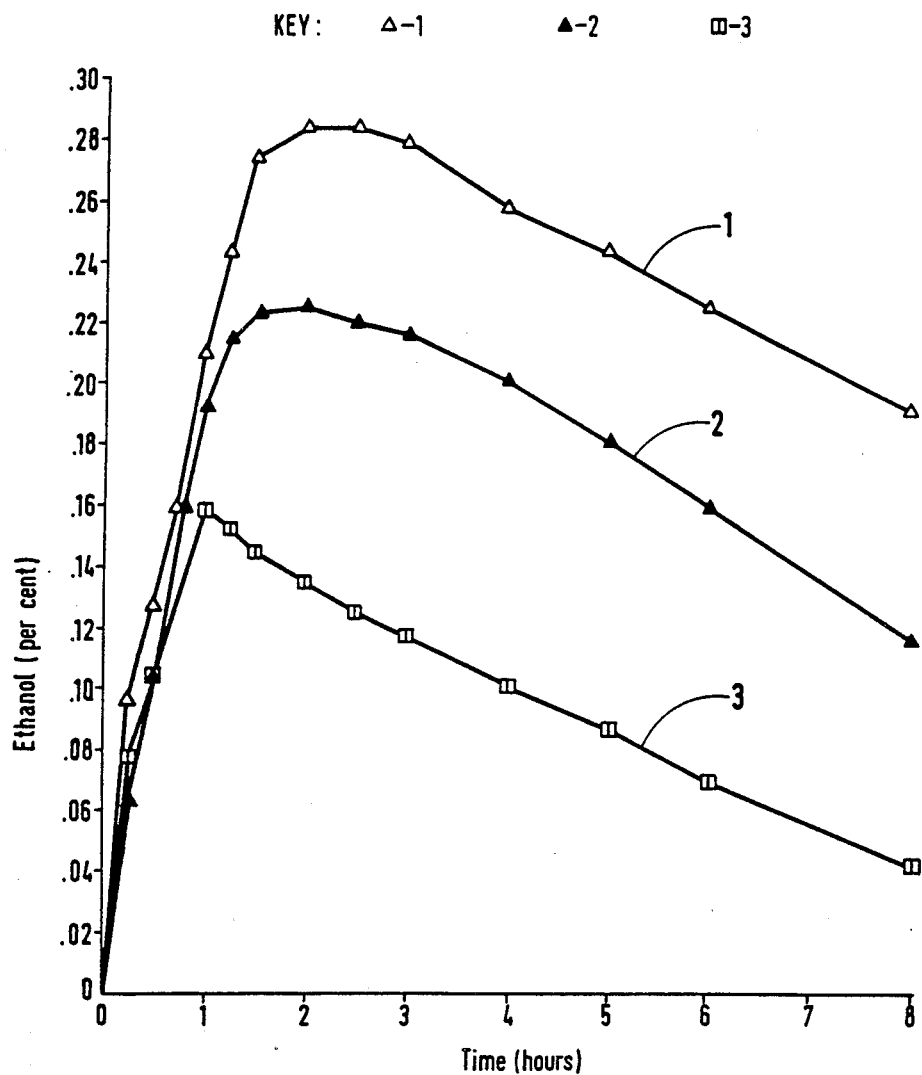

In the FIGS. 1 and 2 there is illustrated the effect of a composition according to the invention on baboons.

The invention will now be illustrated by the tests on baboons.

EXAMPLES

Tests were carried out on baboons these being primates the physiology of which closely resemble man. They were young males each of body weight approximately 5 kg. Silicalite and ZSM 5 were each used as absorbents, with indistinguishable effect from each other. They were dried in vacuo at 100° C. to remove absorbed material, then suspended in water before use. The baboons were fed alcohol and absorbent, each in single doses for each experiment, by gavage after overnight fasting. Drinking water was available ad libitum but access to food was not permitted until four hours after ethanol. Blood samples were taken at intervals and plasma ethanol concentration estimated in the laboratory by a specific and repeatable enzymic method.

EXPERIMENT A

Baboon H896M was fed ethanol 4 ml/kg followed, 2 minutes later, by Silicalite 14 g/kg (kg referring to body weight), each in an equal volume of water. Blood alcohol concentration was plotted for 24 hours. Seven days later this procedure was repeated without the Silicalite. Results:

| Blood Alcohol Concentration (mg/100 ml) | Without Silicalite | With Silicalite |
|---|---|---|
| Peak | 307 | 264 |
| 12 hours after dose | 179 | 84 |
| 24 hours after dose | 13 | Under 4 |

EXPERIMENT B

Baboons H245 and H770 were fed 1.5% (w/v) aqueous carboxymethylcellulose 14 ml/kg followed, 1 minute later, by ethanol 3 ml/kg dissolved in water 6 ml/kg. This was repeated 7 days later with ZSM5 14 g/kg added to the carboxymethylcellulose solution. Results:-

| Blood Alcohol Concentration (mg/100 ml) | | Without ZSM 5 | With ZSM 5 |
|---|---|---|---|
| H 245 | Peak | 258 | 193 |
|  | 8 hours after dose | 141 | 85 |
| H 770 | Peak | 266 | 199 |
|  | 8 hours after dose | 183 | 118 |

ZSM5 reduced the area under the alcohol/time curve from 0–8 hours by 31.3% for baboon H245 and by 25.1% for baboon H770.

EXPERIMENT C

Baboons H245 and H770 were fed 3 ml/kg ethanol dissolved in 6 ml/kg water followed, 1 minute later, by 1.5% (w/v) aqueous carboxymethylcellulose 14 g/kg. This was repeated 7 and 14 days later with Silicalite 14 g/kg added to the carboxymethylcellulose. However, on this occasion the time interval was increased from 1 minute to 1 hour.

The results, shown in FIG. 1 and FIG. 2, clearly demonstrate that the adsorbent was effective even when withheld for 1 hour after the consumption of alcohol.

FIG. 1 illustrates the concentration of ethanol in baboon H245 after an oral dose.
1. Ethanol followed by vehicle (1 minute after ethanol dose).
2. Ethanol followed by silicalite (1 minute after ethanol dose).
3. Ethanol followed by silicalite (1 hour after ethanol dose).

FIG. 2 illustrates the concentration of alcohol in baboon H770 after an oral dose of:
1. Ethanol followed by vehicle (1 minute after ethanol dose).
2. Ethanol followed by silicalite (1 minute after ethanol dose).
3. Ethanol followed by silicalite (1 hour after ethanol dose).

Other than effects directly attributable to alcohol, no untoward clinical effect was observed in the baboons during or after these experiments.

It was noted that the addition of the adsorbent to blood-plasma samples reduced any alcohol content almost instantly. This establishes the feasibility of using the adsorbent in a blood-dialysis machine to remove alcohol, or other small molecules such as solvents and gaseous anaesthetics, from the body for therapeutic purposes.

I claim:

1. A method for reducing the alcohol content of the blood of human beings in need thereof comprising the oral administration of an edible composition comprising a dispersion in an edible or physiologically compatible base of an effective alcohol content-reducing amount of a physiologically inert hydrophobic crystalline essentially silicon and oxygen zeolite of pore size permitting the absorption of ethanol but preventing the absorption of larger molecules with lipophilic character that occur in significant concentration in the digestive system.

2. A method as claimed in claim 1 wherein said hydrophobic crystalline zeolite has a molar ratio of silica to alumina of not less than 12:1.

3. A method as claimed in claim 2 wherein said hydrophobic crystalline zeolite is selected from the group consisting of silicalite and ZSM-5.

4. A method for reducing the alcohol content of the blood of human beings in need thereof comprising the rectal administration of a suppository containing an effective alcohol contenreducing amount of physiologically inert hydrophobic crystalline essentially silicon and oxygen zeolite of pore size permitting the absorption of ethanol but preventing the absorption of larger molecules with lipophilic character that occur in significant concentration in the digestive system.

5. A method as claimed in claim 4 wherein said hydrophobic crystalline zeolite has a high silica content, the molar ratio of silica to alumina being not less than 12:1.

6. A method as claimed in claim 5 wherein said hydrophobic crystalline zeolite is selected from the group consisting of silicalite and ZSM-5.

* * * * *